United States Patent [19]
Mirejovsky et al.

[11] Patent Number: 6,147,122
[45] Date of Patent: Nov. 14, 2000

[54] PROPOFOL COMPOSITION CONTAINING SULFITE

[75] Inventors: Dorla Mirejovsky, Irvine; Liananingsih Tanudarma, Anaheim; Dilip R. Ashtekar, Irvine, all of Calif.

[73] Assignee: Gensia Sincor Inc., Irvine, Calif.

[21] Appl. No.: 09/247,449

[22] Filed: Feb. 10, 1999

Related U.S. Application Data

[63] Continuation-in-part of application No. 09/021,671, Feb. 10, 1998.

[51] Int. Cl.$^7$ ............................ A61K 31/05; A61K 31/10
[52] U.S. Cl. ............................ 514/731; 514/709; 514/712
[58] Field of Search ................................ 514/731, 566, 514/709, 712; 424/346, 80

[56] References Cited

U.S. PATENT DOCUMENTS

| | | | |
|---|---|---|---|
| 4,056,635 | 11/1977 | Glen et al. | 514/731 |
| 4,452,817 | 6/1984 | Glen et al. | 514/730 |
| 4,798,846 | 1/1989 | Glen et al. | 514/731 |
| 5,637,625 | 6/1997 | Haynes. | |
| 5,688,800 | 11/1997 | Nomura et al.. | |
| 5,714,520 | 2/1998 | Jones et al. | 514/731 |
| 5,731,355 | 3/1998 | Jones et al. | 514/731 |
| 5,731,356 | 3/1998 | Jones et al. | 514/731 |
| 5,908,869 | 6/1999 | Jones et al. | 514/731 |

FOREIGN PATENT DOCUMENTS

| | | |
|---|---|---|
| 2 298 789 | 9/1996 | United Kingdom. |
| 97/10814 | 3/1997 | WIPO. |

OTHER PUBLICATIONS

Foulke, et al., "New Food Code" *FDA Consumer* 28(3):7–9 (1994).

Shah, et al.,"Effect of pH, Chlorobutanol, Cysteine Hydrochloride, Ethylenediaminetetraacetic Acid, Propylene Glycol, Sodium Metabisulfite, and Sodium Sulfite on Furosemide Stability in Aqueous Solutions" *J. Pharm. Sci.* 69(5): 594–596 (1980).

*Primary Examiner*—William R. A. Jarvis
*Assistant Examiner*—Vickie Kim

[57] ABSTRACT

Sterile pharmaceutical compositions for parenteral administration containing 2,6-diisopropylphenol (propofol) are described for use as anesthetics. The compositions comprise an oil-in-water emulsion of propofol additionally comprising an amount of sulfite sufficient to prevent significant growth of microorganisms for at least 24 h after adventitious contamination.

80 Claims, 1 Drawing Sheet

PROPOFOL COMPOSITION CONTAINING SULFITE

This application is a continuation-in-part of application Ser. No. 09/021,671, filed Feb. 10, 1998 which is hereby incorporated by reference in its entirety.

FIELD OF THE INVENTION

In one aspect, the present invention relates to new pharmaceutical compositions containing 2,6-diisopropylphenol, known as propofol, and sulfite. In another aspect, the present invention relates to the use of these compositions to induce anesthesia in mammals, including sedation, and the induction and maintenance of general anesthesia. In yet another aspect, the present invention relates to the use of sulfite as a preservative for parenterally administered oil-in-water emulsions, in general. In still another aspect, the present invention relates to a process for the manufacture of oil-in-water emulsions containing sulfite as a preservative.

BACKGROUND OF THE INVENTION 2,6-Diisopropylphenol, generically named propofol, is a well-known and widely-used, injectable anesthetic with hypnotic properties used both as a sedative, and to induce and maintain general anesthesia. It is sold as Diprivan (trademark Zeneca) for human use and Rapinovet (trademark Zeneca) for veterinary use. Propofol is administered directly into the bloodstream either by bolus injection or by infusion. Because the onset of anesthesia is largely controlled by a drug's diffusion rate through the blood-brain barrier, propofol's lipophilicity is key to its rapid activity. This lipophilicity, however, renders propofol relatively insoluble in water, hence it must be administered in conjunction with solubilizing agents, surfactants, or solvents; or as oil-in-water emulsions (Jones et al. (1998) U.S. Pat. No. 5,714,520). All references cited herein are incorporated by reference in their entirety.

As a parenterally administered agent, sterility of propofol formulations is essential. Commercial formulations are oil-in-water emulsions containing approximately 1% –2% propofol in 10% soybean oil. These formulations also typically contain a surfactant, 1.2% egg phosphatide for example, 2.25% glycerol to make the formulation isotonic, sodium hydroxide to adjust the pH to physiological pH, and 0.005% EDTA equivalent (as edetate) to retard microbiological growth (all weights approximate) (Id.). Edetate containing formulations are not antimicrobially preserved by USP standards; however, microbial growth is retarded (Id.).

Non-preserved, propofol oil-in-water emulsion formulations have significant drawbacks arising from the fact that these formulations support microbial growth: strict aseptic handling technique is required; maximum utility time is 12 h maximum after vial entry. Handling recommendations include immediate administration after vial entry, and disposal of infusion assemblies and of unused material after 12 h. Nevertheless, reports of nosocomial infections resulting from adventitious contamination are not uncommon (Bennett et al. (1995) N. Engl. J. Med. 333:147–154). Improper handling techniques include delayed administration after transfer from vial to syringe, use of 50–and 100–mL products as multi-use, for multiple patients, and use of 50 and 100 mL products for an extended time period.

An application for which preserved propofol formulations are particularly advantageous is their use as a long-term sedative by continuous infusion. The risk of microbial contamination of non-preserved propofol in infusion devices increases both with residency-time in the infusion device, and with increased manipulation of the device. The utility time of formulations containing EDTA salts (edetates) is at least 24 h compared to 6 to 12 h for non-preserved formulations (Jones et al.). A longer lasting formulation means that fewer manipulations are required. The consequent reduced manipulation accrues a number of important benefits: reduced probability of microbial contamination, reduced probability of operator error, reduced drug waste, and reduced labor intensiveness—all of which combine to increase safety and reduce costs.

SUMMARY OF THE INVENTION

An extensive and vigorous evaluation of known antimicrobial agents for parenteral products led to the unexpected discovery that sulfite can be included in an oil-in-water emulsion of propofol in a non-toxic amount which is soluble in the aqueous phase and does not partition into the organic phase, and which retards or suppresses the of growth of likely microbial contaminants, without destabilizing the emulsion and without adversely reacting with other formulation components. These results are especially surprising in light of published data indicating that sodium metabisulfite is completely ineffectual for this particular application (1% Diprivan (Zeneca) 0.1% $Na_2S_2O_5$) (Jones et al.).

Sodium metabisulfite is a salt of a sulfurous acid (formally, metasulfurous acid). The present invention includes all pharmaceutically acceptable derivatives of sulfurous acid (orthosulfurous acid) and metasulfurous acid approved by the FDA for human use (sulfites) and any combinations thereof. These compounds include, but are not limited to, sodium sulfite, sodium bisulfite, potassium sulfite, potassium bisulfite, sodium metabisulfite, and potassium metabisulfite.

Accordingly, the present invention provides a sterile composition for parenteral administration comprising an oil-in-water emulsion in which propofol is dissolved in a water-immiscible solvent that is emulsified with water wherein said emulsion is stabilized by means of a surfactant. The composition further comprises an amount of a sulfite sufficient to exhibit antimicrobial activity against microorganisms most likely to contaminate the propofol preparation.

The present invention also includes the use of sulfites as preservatives for any sterile, parenterally administered oil-in-water emulsion. In addition to propofol compositions, such formulations include total-parenteral-nutrition formulations, or oil-in-water vehicles for other pharmaceutical or therapeutic agents.

Additionally, the present invention includes a process for the manufacture of sterile, propofol oil-in-water emulsions for parenteral administration comprising propofol dissolved into a water-immiscible liquid emulsified with water, wherein said emulsion is stabilized by means of a surfactant and further comprising effective amounts of sulfite as a preservative. Timing of the addition of the sulfite and control of the process temperature are both critical to the maintenance of antimicrobial activity in the composition. This aspect of the invention may be advantageously applied to other drugs formulated as an oil-in water emulsion.

DEFINITIONS

In accordance with the present invention and as used herein, the following terms are defined to have the following meanings, unless explicitly stated otherwise:

The term "edetate" refers to an anion derived from deprotonation of EDTA. EDTA is a tetrabasic acid, thus an edetate may be mono-, di-, tri- or tetraanionic. The term "edetate" may also refer to a salt of an edetate anion.

The term "oil-in-water emulsion" refers to a distinct two phase system that is in equilibrium and in effect, as a whole, is kinetically stable and thermodynamically unstable.

The term "preservative" refers to an agent or agents that suppress or prevent microbiological growth at 24 h by no more than 10-fold compared to time-zero.

The term "sulfite" refers to all pharmaceutically acceptable derivatives of sulfurous acid (orthosulfurous acid) and metasulfurous acid approved by the FDA now or in the future for human use. These compounds include sodium sulfite, sodium bisulfite, potassium sulfite, potassium bisulfite, sodium metabisulfite, and potassium metabisulfite.

DETAILED DESCRIPTION OF THE INVENTION

Development of a preservative-containing, oil-in-water emulsion formulations is a daunting task. Key requirements for the preservative include:

a. Soluble in the aqueous phase, does not partition into the organic phase;

b. Low toxicity, since large volumes are commonly used;

c. Retardation/suppression of growth of likely microbial contaminants;

d. Compatibility with all other formulation components;

e. Not destabilizing of the emulsion.

Many currently used preservatives are lipophilic, and hence, would be ineffective for use in oil-in-water emulsions because of requirement a. Emulsion physical stability and clinical performance depend critically on the particle-size distribution and the number of large particles (requirement e) (Dabbah et al. (1995) in USP Open Conference-Microbiological Compendial Issues The United States Pharmacopeial Convention, pp 87–96).

Sodium metabisulfite, sodium bisulfite, sodium sulfite, potassium metabisulfite, and potassium sulfite are used in many parenteral formulations as antioxidants and/or antimicrobials in concentrations of 0.025–0.66%. The antimicrobial activity, however, requires a pH in the 2.5–5.5 range. Oil-in-water emulsions, on the other hand, are typically formulated at pH 6–9 to assure the ionization of the headgroups of the phospholipid surfactants incorporated therein. The resulting electrostatic repulsion favors the formation of small oil particles and discourages their coalescence with time. We have discovered stable emulsions containing each of the above sulfite-containing compounds in the 4.5–6.4 pH range that nevertheless exhibit antimicrobial activity. We have also discovered a process for the manufacture of these emulsions which minimizes the loss of the sulfite-containing compounds through autooxidation.

While not wishing to be limited to this mechanism, the inventors believe that the inhibition and destruction of microorganisms by sodium metabisulfite, sodium bisulfite, sodium sulfite, potassium metabisulfite, and potassium sulfite is highest at lower pH values. The primary activity of these compounds is believed to be due to the formation of sulfurous acid ($H_2SO_3$) and bisulfite ions. The antimicrobial action is believed to be due to inhibition of enzyme systems, especially through oxidation of SH groups in enzymes and proteins. The bisulfite ions may also interact with pyrimidine bases (Foegeding, P. M. and Busta, F. F. "Chemical Food Preservatives," pp 802–832, in *Disinfection, Sterilization, and Preservation*, fourth edition, Ed S.S. Block, 1991, Pub. Lea and Febiger, William and Wilkins, Philadelphia, USA).

1. Pharmaceutical Compositions

The composition of the present invention comprises a sulfite, preferably a salt of metasulfurous acid. More preferably, the sulfite is sodium metabisulfite and other sulfurous acid salts such as sodium bisulfite, sodium sulfite, potassium metabisulfite, or potassium sulfite. The sulfite will typically be present from about 0.0075% to about 0.66% weight. Preferably, the sulfite is present in the range of about 0.0075% to about 0.1% weight and most preferably about 0.025% weight. It will be apparent to one skilled in the pharmaceutical arts that other sulfites may be used in these compositions and that their weight percentages will depend on the particular sulfite used.

Maximal dosages of sulfite will occur in long-term infusion situations, for example when used as a sedative. Typical dosages of propofol are 0.3–3 mg/kg/h, but may range to 10 mg/kg/h in exceptional cases, equivalent to 1.68 L emulsion/day/70 kg. Under these conditions, the total sulfite administered is well below the limit set by the World Health Organization (WHO) (7.0 mg/kg as $SO_2$) and is below the amount infused in total-parenteral-nutrition amino acid formulations, as well as during peritoneal dialysis (Gunnison and Jacobsen (1987) Crit. Rev. Toxicol. 17:185–214).

The composition of the present invention typically comprises 0.1 to 5% weight propofol. Preferable compositions comprise from about 1% to about 2% weight propofol. More preferable compositions are about 1% weight and about 2% weight propofol. The propofol may be dissolved in a pharmaceutically acceptable water-immiscible solvent and emulsified in water and said emulsion stabilized by means of a surfactant; or the propofol may itself be emulsified in water without addition of a water-immiscible solvent and said emulsion stabilized by means of a surfactant.

Water-immiscible solvents suitable for the preparation of oil-in-water emulsions suitable for parenteral administration are known to those skilled in the pharmaceutical arts (*Handbook of Pharmaceutical Exipients* Wade and Weller, Eds. (1994) American Pharmaceutical Association, The Pharmaceutical Press: London, pp 451–453). Typically, the water-immiscible solvent will be a vegetable oil: for example, soybean, safflower, cottonseed, corn, sunflower, arachis, and castor. The water-immiscible solvent may also be a wholly or partially manufactured material, for example mono-, di-, and triglycerides, fatty acid esters, or chemically and/or physically modified vegetable oils. The present invention may also comprise any combination of said water-immiscible solvents. When used, the water-insoluble solvent comprises up to about 30% weight of the composition, preferably in the range of about 5% to about 25% weight, more preferably in the range of about 10% to about 20% weight, most preferably about 10% weight.

The composition of the present invention comprises a pharmaceutically acceptable surfactant which aids in the emulsification of the water-immiscible phase in water and stabilizes said emulsion (Id.). Suitable surfactants include naturally occurring surfactants: for example, egg or soy phosphatides, either in their native or modified forms; manufactured non-ionic surfactants, for example a polyethylene glycol or esters thereof; or any mixture thereof. Preferable surfactants are egg or soy phosphatides, for example egg-yolk phospholipid. The amount of surfactant effective in producing and maintaining a stable oil-in-water emulsion will depend the particular formulation. The factors and their relationships are well known to skilled practitioners in the pharmaceutical arts. These factors include the presence or absence of a water-immiscible solvent, the particular water-immiscible solvent used, the particular surfactant employed, the presence of salts, and the pH of the composition.

Preferably, the total number of fat globules/0.1 mL in the 1–20 μm particle size range is ≦600,000 and in the 5–20 μm particle size range is ≦200,000. Preferably, the % volume of total fat globules/0.1 mL in the 1–20 μm particle size range is ≦0.3 and is ≦0.2 in the 5–20 μm size range. Preferably, the mean fat globule size is less than 500 nm, and more preferably less than 250 nm.

The composition of the present invention is formulated with pH in the range of about 4.5 to about 6.4. The pH may be adjusted as required by means of addition of an alkali, for example sodium hydroxide, or an acid, for example hydrochloric acid.

The composition of the present invention may be made isotonic with blood by incorporation of a suitable tonicity modifier, for example glycerin (Id.).

The compositions of the present invention are sterile, aqueous formulations and are prepared by standard manufacturing techniques using, for example, aseptic manufacturing methods and sterilization by autoclaving.

Compositions of the current invention may be formulated to match commercial formulations in clinical performance and physical properties. Tables 1 below compares the composition of the preferred embodiment of the present invention with Diprivan. Table 2 below compares the physical properties of these two formulations.

TABLE 1

Comparison the formulation of a composition of the present invention with a commercial formulation.

| Component | Propofol Injectable Emulsion 1% | DIPRIVAN Injectable Emulsion 1% |
| --- | --- | --- |
| Propofol, mg/mL | 10 | 10 |
| Soybean oil, mg/mL | 100 | 100 |
| Glycerin, mg/mL | 22.5 | 22.5 |
| Egg-yolk phospholipid, mg/mL | 12 | 12 |
| Disodium edetate, mg/mL | — | 0.05 |
| Sodium metabisulfite, mg/mL | 0.25 | — |
| WFI q.s. to 1 mL | | |
| pH | 4.5–6.4 | 7.0–8.5 |

Diprivan trademark of Zeneca.

TABLE 2

Comparison of physical properties of a composition of the present invention with a commercial formulation.

| Physico-Chemical Parameter | Propofol Injectable Emulsion 1% | DIPRIVAN Injectable Emulsion 1% |
| --- | --- | --- |
| Appearance | White emulsion with no visible oil droplets | White emulsion with no visible oil droplets |
| Density | 0.995 | 0.995 |

TABLE 2-continued

Comparison of physical properties of a composition of the present invention with a commercial formulation.

| Physico-Chemical Parameter | Propofol Injectable Emulsion 1% | DIPRIVAN Injectable Emulsion 1% |
| --- | --- | --- |
| Osmolality, mg/mL | 300 | 300 |
| Viscosity, centistokes | 1.6 | 1.6–1.7 |

Diprivan trademark of Zeneca.

The following Table 3 shows that the particle size distribution of the emulsion containing sodium metabisulfite, sodium bisulfite, sodium sulfite, postassium metabisulfite, or potassium sulfite are comparable to the Zeneca product containing 0.005% EDTA. The data show that the addition of any of the salts did not cause an increase in the number of large particles which is a concern for injectable emulsions.

The size of particles with a submicron diameter (<1 μm) is monitored using Nicomp 370, manufactured by Particle Sizing Systems, Santa Barbara, Calif. This instrument measures an apparent average particle size and distribution. The size and the number of fat globules larger than 1μm are determined using the AccuSizer™ 770 manufactured by Particle Sizing Systems, Santa Barbara, California. This technique allows separate monitoring of the number of particles and % volume of the oil taken by these particles for the 1–20 μm and 5–20 μm diameter ranges.

TABLE 3

| | Total Number of Fat Globules/0.1 mL | | % Volume of Total Fat Globules/0.1 mL | | Mean Fat |
| --- | --- | --- | --- | --- | --- |
| | Particle Size 1–20 μm | Particle Size 5–20 μm | Particle Size 1–20 μm | Particle Size 5–20 μm | Globule Size nm |
| Diprivan Injectable Emulsion 1% (Average of 3 different lots) | 312,911 ± 117,479 | 17,095 ± 6,398 | 0.050 ± 0.019 | 0.025 ± 0.010 | 194 ± 6 |
| Propofol Injectable Emulsion 0.025% Sodium Metabisulfite (Average of 2 different lots) | 311,894 ± 71,940 | 3,122 ± 642 | 0.022 ± 0.005 | 0.009 ± 0.002 | 198 ± 2 |
| Propofol Injectable Emulsion (0.025%) of: | | | | | |
| Sodium Bisulfite | 100,691 | 3,347 | 0.012 | 0.004 | 201 |
| Sodium Sulfite | 128,338 | 6,689 | 0.021 | 0.010 | 239 |
| Potassium Metabisulfite | 156,569 | 6,470 | 0.022 | 0.011 | 197 |
| Potassium Sulfite | 50,151 | 1,716 | 0.006 | 0.005 | 202 |

The compositions of the present invention are useful as anesthetics including sedation, and induction and maintenance of general anesthesia. Thus, in another aspect, the present invention provides a method for inducing anesthesia in mammals which comprises parenteral administration of a sterile, aqueous pharmaceutical composition comprising an oil-in-water emulsion in which propofol, either alone or dissolved in a water-immiscible solvent, is emulsified in water, wherein said emulsion is stabilized by means of a surfactant; which further comprises an effective amount of sulfite.

Dosage levels appropriate for the induction of desired degree of anesthesia, for example sedation, or induction of or maintenance of general anesthesia, by the compositions of the present invention will depend on the type of mammal under treatment and the physical characteristics of the specific mammal under consideration. These factors and their relationship in determining this amount are well known to skilled practitioners in the medical arts. Approximate dosage levels may be derived from the substantial literature on propofol, may be tailored to achieve optimal efficiency, and will be contingent on myriad factors recognized by those skilled in the medical arts including weight, diet, and concurrent medication.

The antimicrobial effects of sulfites may also be advantageously applied to other sterile, oil-in-water emulsions for parenteral administration. Examples include total-parenteral-nutrition formulations and oil-in-water emulsions of other pharmaceuticals or therapeutic agents.

Oil-in-water emulsion total-parenteral-nutrition formulations are administered by infusion to patients for whom oral nutrition is impossible, undesirable, or insufficient. The emulsified lipids provide a concentrated caloric content. These formulations may also contain other nutrients, for example amino acids, vitamins, and minerals. Commercial examples of such formulations include Intralipid (trademark Pharmacia), Lipofundin (trademark Braun), and Travamulsion (trademark Baxter). Accordingly, the present invention provides a sterile total-parenteral-nutrition formulation comprising lipids or fats emulsified in water which further comprises an effective amount of sulfite as a preservative.

A wide variety of current and potential pharmaceutical or therapeutic agents are highly lipophilic, for example steroids, prostaglandins, leukotrienes, and fat-soluble vitamins. Such compounds may be advantageously administered in oil-in-water emulsion vehicles comprising a sulfite as a preservative, particularly when administration will occur over an extended period. Accordingly, the present invention provides a sterile, therapeutic composition comprising a lipophilic pharmaceutical or therapeutic agent, either alone or dissolved in a water-immiscible solvent, emulsified in water, which further comprises an amount of sulfite effective as a preservative.

2. Process for Manufacture

Figure 1:
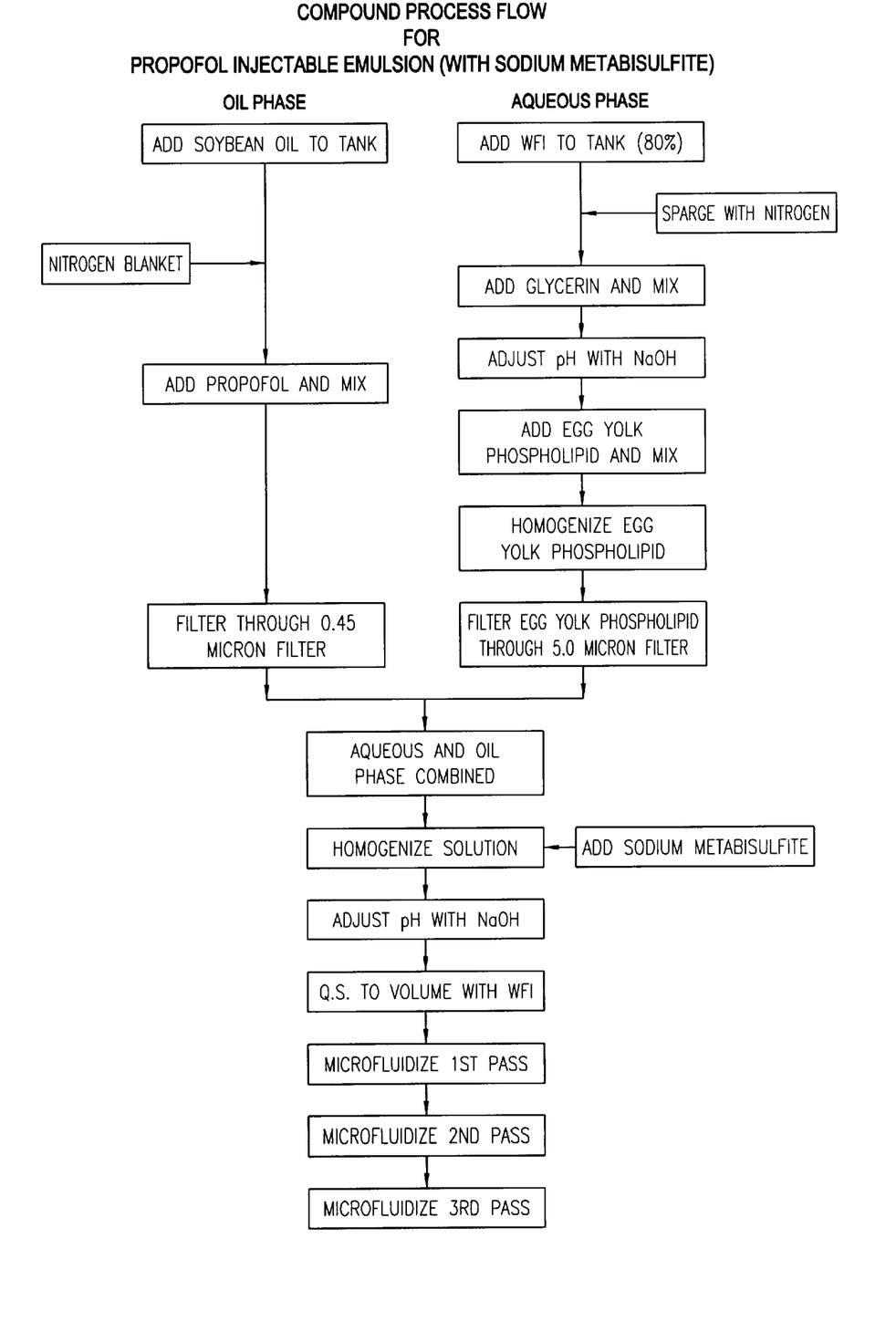
FIG. 1. Flow chart for the manufacturing process for sterile propofol oil-in-water emulsion formulations containing sodium metabisulfite.

A scheme for the manufacture of compositions of the present invention is shown in FIG. 1. The present invention provides a process for manufacturing the compositions of the present invention comprising the steps of:

1. Preparing an aqueous phase by adding glycerin and sodium hydroxide into about 80% WFI in a compounding tank while maintaining the temperature at approximately 40° C.;
2. Adding the egg-yolk phospholipid to said aqueous phase;
3. Homogenizing said aqueous phase;
4. Filtering said aqueous phase through a 5.0 µm filter;
5. Preparing an oil phase by dissolving propofol in soybean oil;
6. Filtering said oil phase through a 0.45 µm filter;
7. Combining and homogenizing said aqueous and oil phases;
8. Adding a solution of a sulfite compound dissolved in WFI near the end of the homogenization step;
9. Adding sodium hydroxide or hydrochloric acid solution to adjust the pH;
10. Adjusting to specified volume with WFI;
11. Microfluidizing the crude emulsion to the target globule size and particle size distribution while maintaining the temperature at about 30° C.;
12. Filtering the propofol oil-in-water emulsion into a filling vessel;
13. Filling and sealing containers under nitrogen;
14. Autoclaving said containers.

Typically, 12 mg/L of sodium hydroxide is added in step 3. Preferably, all steps are performed under a nitrogen atmosphere.

Timing of the addition of the sulfite is critical. If dissolved in the aqueous phase in step 3 or 4, the antimicrobial activity is lost, presumably from loss of bisulfite during processing. Optimal antimicrobial activity was obtained when the sulfite was added at step 10. Typically, the sulfite is added by a stock solution of about 54 g/L after 25 minutes of homogenization. Typically, the mixture is homogenized for an additional 5 minutes. Furthermore, the thermal lability and sensitivity to oxidation of the sulfites necessitate accurate temperature control and a nitrogen or other inert gas environment in the manufacturing process.

This procedure may be modified to prepare other compositions of the present invention by substituting other water immiscible solvents for the soybean oil, other surfactants for the egg yolk phospholipid, other acids or bases to adjust the pH instead of sodium hydroxide, and/or other tonicity modifiers for the glycerin. The procedure may also be modified to prepare other drugs in a preserved oil-in-water emulsion or those for parenteral nutrition.

3. Microbiological Activity

The growth retarding capability of 1% propofol injectable emulsion containing sodium metabisulfite, sodium bisulfite, sodium sulfite, potassium metabisulfite, or potassium sulfite were evaluated using membrane filtration technique and broth cultures. Approximately 50–200 colony forming units (CFU) per mL of four standard organisms recommended by United States Pharmacopeia (USP) for preservative efficacy tests were inoculated in each formulation. These four organisms are identified as Staphylococcus aureus (ATCC 6538), *Escherichia coli* (ATCC 8739), *Pseudomonas æruginosa* (ATCC 9027), and *Candida albicans* (ATCC 10231). In addition to these organisms, S. epidermidis (ATCC 12228) and S. aureus (coagulase negative, ATCC 27734) were also tested.

The antimicrobial activity of propofol containing sodium metabisulfite was compared with propofol containing 0.005% disodium ethylenediaminetetraacetic acid (Diprivan EDTA, trademark Zeneca), and a control propofol formulation lacking preservative. After the inoculation of the test organisms, test formulations were incubated at 30–35° C. The viable count of the test organism was determined immediately following the inoculation and after 24 h of incubation at 30–35° C. Each datum for the metabisulfite composition is the average of eight determinations performed on two fresh 20-mL vials, two 1-month stability 20-mL vials, two fresh 100-mL vials, and two 1-month stability 100-mL vials. The Diprivan samples were from four fresh 50-mL vials. Unpreserved propofol samples contained the same ingredients, except they contained no preservatives. The preservative was considered effective if the microbial growth was suppressed, or allowed for a no-more-than 10-fold increase in growth as compared to the zero-hour viable count (count of the organism immediately following inoculation) of each of the test organisms.

The following Tables 4–12 compare the antimicrobial effectiveness of sodium metabisulfite and other sulfite formulations with that of Diprivan and unpreserved propofol. These results indicate that sodium metabisulfite and the other sulfite compounds are competent to prevent the significant growth of microorganisms for at least 24 h after adventitious, extrinsic contamination.

TABLE 4

Comparison of microbial growth retarding activity of various formulations against *S. aureus* (ATCC 6538).

| Formulation | Viable count of survivors $\log_{10}$ CFU/mL ± SD | | Decrease in survivors |
|---|---|---|---|
| (number of samples) | 0 h | 24 h | $\log_{10}$ CFU/mL |
| Propofol metabisulfite (8) | 2.08 ± 0.28 | ND | 2.08 |
| Diprivan EDTA (4) | 2.37 ± 0.26 | 1.55 ± 0.58 | 0.82 |
| Unpreserved Propofol (2) | 2.0 | 5.5 | NA |

NA: Not applicable. ND: No viable organisms detected in 1-mL aliquot. SD: standard deviation.

TABLE 5

Comparison of microbial growth retarding activity of various formulations against *S. epidermidis* (ATCC 12228).

| Formulation | Viable count of survivors $\log_{10}$ CFU/mL ± SD | | Decrease in survivors |
|---|---|---|---|
| (number of samples) | 0 h | 24 h | $\log_{10}$ CFU/mL |
| Propofol metabisulfite (8) | 2.27 ± 0.04 | ND | 2.27 |
| Diprivan EDTA (4) | 2.20 ± 0.34 | 1.05 ± 0.35 | 1.15 |
| Unpreserved Propofol | 2.4 | 4.55 ± 0.07 | NA |

NA: Not applicable. ND: No viable organisms detected in 1-mL aliquot. SD: standard deviation.

TABLE 6

Comparison of microbial growth retarding activity against *E. coli* (ATCC 8739) of various formulations.

| Formulation | Viable count of survivors $\log_{10}$ CFU/mL ± SD | | Decrease in survivors |
|---|---|---|---|
| (number of samples) | 0 h | 24 h | $\log_{10}$ CFU/mL |
| Propofol metabisulfite (8) | 2.26 ± 0.05 | 2.28 ± 0.13 | NA |
| Diprivan EDTA (4) | 2.37 ± 0.09 | 0.275 ± 0.55 | 2.095 |
| Unpreserved Propofol | 2.3 | 7.25 ± 0.07 | NA |

NA: Not applicable. ND: No viable organisms detected in 1-mL aliquot. SD: standard deviation.

TABLE 7

Comparison of microbial growth retarding activity of various formulations against *P. aeruginosa* (ATCC 8739).

| Formulation | Viable count of survivors $\log_{10}$ CFU/mL ± SD | | Decrease in survivors |
|---|---|---|---|
| (number of samples) | 0 h | 24 h | $\log_{10}$ CFU/mL |
| Propofol metabisulfite (8) | 1.97 ± 0.26 | ND | 1.97 |
| Diprivan EDTA (4) | 1.97 ± 0.17 | 2.50 ± 0.47 | NA |
| Unpreserved Propofol | 2.35 ± 0.07 | 6.8 | NA |

NA: Not applicable. ND: No viable organisms detected in 1-mL aliquot. SD: standard deviation.

TABLE 8

Comparison of microbial growth retarding activity against *S. aureus* (coagulase negative, ATCC 27734) of various formulations.

| Formulation | Viable count of survivors $\log_{10}$ CFU/mL ± SD | | Decrease in survivors |
|---|---|---|---|
| (number of samples) | 0 h | 24 h | $\log_{10}$ CFU/mL |
| Propofol metabisulfite (8) | 2.28 ± 0.22 | ND | 2.28 |
| Diprivan EDTA (4) | 2.87 ± 0.05 | 2.07 ± 0.28 | 0.80 |
| Unpreserved Propofol | 3.15 ± 0.07 | 7.05 ± 0.07 | NA |

NA: Not applicable. ND: No viable organisms detected in 1-mL aliquot. SD: standard deviation.

TABLE 9

Comparison of microbial growth retarding activity against *C. albicans* (ATCC 10231) of various formulations.

| Formulation | Viable count of survivors $\log_{10}$ CFU/mL ± SD | | Decrease in survivors |
|---|---|---|---|
| (number of samples) | 0 h | 24 h | $\log_{10}$ CFU/mL |
| Propofol metabisulfite (8) | 2.42 ± 0.08 | 3.13 ± 0.22 | NA |
| Diprivan EDTA (4) | 2.30 ± 0.08 | 3.20 ± 0.28 | NA |
| Unpreserved Propofol | 2.3 | 5.10 ± 0.14 | NA |

NA: Not applicable. ND: No viable organisms detected in 1-mL aliquot. SD: standard deviation.

TABLE 10

Comparison of microbial growth retarding activity against *E. coli* (ATCC 8739) of various sulfite-containing propofol injectable emulsion formulations (0.025%).

| Formulations | Viable count of survivors $\log_{10}$ CFU/mL ± SD | | Decrease in survivors |
|---|---|---|---|
|  | 0 h | 24 h | $\log_{10}$ CFU/mL |
| Propofol injectable emulsion with: | | | |
| Sodium bisulfite | 2.3 | 1.7 | 0.6 |
|  | 2.3 | 2.2 | 0.1 |
| Sodium sulfite | 2.3 | 1.3 | 1.0 |
|  | 2.3 | 1.4 | 0.9 |

TABLE 10-continued

Comparison of microbial growth retarding activity against *E. coli* (ATCC 8739) of various sulfite-containing propofol injectable emulsion formulations (0.025%).

| Formulations | Viable count of survivors log$_{10}$ CFU/mL ± SD | | Decrease in survivors log$_{10}$ CFU/mL |
|---|---|---|---|
| | 0 h | 24 h | |
| Potassium metabisulfite | 2.3 | 2.0 | 0.3 |
| | 2.3 | 2.0 | 0.3 |
| Potassium sulfite[1] | 2.3 | 4.8 | NA |
| | 2.3 | 4.7 | NA |
| Diprivan (50 ml) | 2.5 | 0.5 | 2.0 |
| | 2.5 | 0.3 | 2.2 |
| Propofol without antimicrobial agent | 2.3 | 7.3 | NA |

NA: Not applicable. ND: No viable organisms detected in 1-mL aliquot. SD: standard deviation.
[1]Formulation contained 0.03 mg/mL or 0.003% potassium sulfite. The inventors believe that a higher level of potassium sulfite will improve the inhibition of microbial growth.

TABLE 11

Comparison of microbial growth retarding activity against *C. albicans* (ATCC 10231) of various sulfite-containing propofol injectable emulsion formulations (0.025%).

| Formulations | Viable count of survivors log$_{10}$ CFU/mL ± SD | | Decrease in survivors log$_{10}$ CFU/mL |
|---|---|---|---|
| | 0 h | 24 h | |
| Propofol injectable emulsion with: | | | |
| Sodium bisulfite | 2.3 | 1.6 | 0.7 |
| | 2.3 | 1.4 | 0.9 |
| Sodium sulfite | 2.3 | ND | 2.3 |
| | 2.3 | ND | 2.3 |
| Potassium metabisulfite | 2.2 | 1.8 | 0.4 |
| | 2.3 | 2.0 | 0.3 |
| Potassium sulfite[2] | 2.5 | 4.5 | NA |
| | 2.4 | 4.5 | NA |
| Diprivan (50 mL) | 2.5 | 3.4 | NA |
| | 2.5 | 3.4 | NA |
| Propofol without antimicrobial agent | 2.3 | 5.1 | NA |

NA: Not applicable. ND: No viable organisms detected in 1-mL aliquot. SD: standard deviation.
[2]Formulation contained 0.03 mg/mL or 0.003% potassium sulfite. The inventors believe that a higher level of potassium sulfite will improve the inhibition of microbial growth.

TABLE 12

Comparison of microbial growth retarding activity against *P. aeruginosa* (ATCC 9027) of various sulfite-containing propofol injectable emulsion formulations (0.025%).

| Formulations | Viable count of survivors log$_{10}$ CFU/mL ± SD | | Decrease in survivors log$_{10}$ CFU/mL |
|---|---|---|---|
| | 0 h | 24 h | |
| Propofol injectable emulsion with: | | | |
| Sodium bisulfite | 1.8 | ND | 1.8 |
| | 1.8 | ND | 1.8 |

TABLE 12-continued

Comparison of microbial growth retarding activity against *P. aeruginosa* (ATCC 9027) of various sulfite-containing propofol injectable emulsion formulations (0.025%).

| Formulations | Viable count of survivors log$_{10}$ CFU/mL ± SD | | Decrease in survivors log$_{10}$ CFU/mL |
|---|---|---|---|
| | 0 h | 24 h | |
| Sodium sulfite | 1.5 | ND | 1.5 |
| | 1.4 | ND | 1.4 |
| Potassium metabisulfite | 2.4 | ND | 2.4 |
| | 2.4 | ND | 2.4 |
| Potassium sulfite[3] | 2.3 | ND | 2.3 |
| | 2.3 | ND | 2.3 |
| Diprivan (50 mL) | 2.5 | 3.4 | NA |
| | 2.4 | 3.3 | NA |
| Propofol without antimicrobial agent | 2.4 | 6.8 | NA |

NA: Not applicable. ND: No viable organisms detected in 1-mL aliquot. SD: standard deviation.
[3]Formulation contained 0.03 mg/mL or 0.003% potassium sulfite. In spite of this low concentration, the potassium sulfite was still effective in inhibiting growth of *P. aeruginosa*.

The present invention provides a sterile pharmaceutical preparation of propofol that comprises an amount of sulfite sufficient to significantly prevent the growth, or prevent no more than 10-fold increase in growth of each of *S. aureus* (ATCC 6538), *E. coli* (ATCC 8739), P. æruginosa (ATCC 9027), and *C. albicans* (ATCC 10231) *S. epidermidis* (ATCC 12228) and *S. aureus* (coagulase negative, ATCC 27734). Preferably, the sulfite is sodium metabisulfite, sodium bisulfite, sodium sulfite, potassium metabisulfite, or potassium sulfite. Furthermore, in the event of improper aseptic handling of the finished product leading to an accidental extrinsic contamination, the present formulation will suppress, minimize, or limit the chance of microbial growth for at least 24 h.

EXAMPLES

Preferred compositions are as follows:
1% propofol emulsion for injection:
 a. about 1% propofol;
 b. about 10% weight soybean oil;
 c. about 2.25% weight glycerin;
 d. about 1.2% weight egg-yolk phospholipid;
 e. about 0.025% weight sulfite;
 f. sodium hydroxide;
 g. water to 100%.
2% propofol emulsion for injection:
 a. about 2% propofol;
 b. about 10% weight soybean oil;
 c. about 2.25% weight glycerin;
 d. about 1.2% weight egg-yolk phospholipid;
 e. about 0.025% weight sulfite;
 f. sodium hydroxide;
 g. water to 100%.
Preferably, these formulations have pH of approximately 4.5–6.4.

The above examples of compositions, and methods of manufacturing same are exemplary and the invention is not limited solely to those examples.

We claim:
1. A sterile, pharmaceutical composition for parenteral administration which comprises an oil-in-water emulsion in which propofol is dissolved in a water-immiscible solvent, is emulsified with water, and is stabilized by means of a surfactant, and which further comprises an amount of sulfite sufficient to prevent a no more than 10-fold increase in the growth of each of *Staphylococcus aureus* (ATCC 6538), *Escherichia coli* (ATCC 8739), *Pseudomonas æruginosa* (ATCC 9027), and *Candida albicans* (ATCC 10231) for at least 24 h as measured by a test wherein a washed suspension of each organism is added to a separate aliquot of said composition at approximately 50 colony-forming units per mL and incubated at a temperature in the range 30–35° C. and are tested for viable counts of said organisms after 24 h, and wherein said amount of sulfite is less than 0.1% weight of said composition.

2. The sterile, pharmaceutical composition according to claim 1 wherein the sulfite is selected from the group consisting of sodium metabisulfite, sodium sulfite, sodium bisulfite, potassium metabisulfite, and potassium sulfite.

3. The sterile, pharmaceutical composition according to claim 2 wherein said sulfite is sodium metabisulfite.

4. The sterile, pharmaceutical composition according to claim 1 which comprises up to about 30% weight of a water-immiscible solvent.

5. The sterile, pharmaceutical composition according to claim 4 which comprises from about 10% to about 20% weight of a water-immiscible solvent.

6. The sterile, pharmaceutical composition according to claim 1 wherein the water-immiscible solvent is a vegetable oil or ester of a fatty acid.

7. The sterile, pharmaceutical composition according to claim 6 wherein the vegetable oil is soybean oil.

8. The sterile, pharmaceutical composition according to claim 1 wherein the surfactant is a naturally occurring phosphatide.

9. The sterile, pharmaceutical composition according to claim 8 wherein the phosphatide is egg phosphatide or soy phosphatide.

10. The sterile, pharmaceutical composition according to claim 1 wherein the pH is between about 4.5 to about 6.4.

11. The sterile, pharmaceutical composition according to claim 10 wherein sodium hydroxide is present.

12. The sterile, pharmaceutical composition according to claim 1 which is isotonic with blood.

13. The sterile, pharmaceutical composition according to claim 12 which is made isotonic with blood by incorporation of glycerin.

14. The sterile, pharmaceutical composition according to claim 1 which comprises from about 1% to about 2% weight propofol.

15. The sterile, pharmaceutical composition according to claim 14 which comprises about 1% weight propofol.

16. The sterile, pharmaceutical composition according to claim 14 which comprises about 2% weight propofol.

17. A sterile, pharmaceutical composition for parenteral administration which comprises an oil-in-water emulsion in which propofol is dissolved in a water-immiscible solvent, is emulsified with water, and is stabilized by means of a surfactant, and which further comprises an amount of sulfite wherein the amount of sulfite is in the range of about 0.0075% to less than 0.1% weight.

18. The sterile, pharmaceutical composition according to claim 17 wherein the amount of sulfite is about 0.025% weight.

19. The sterile, pharmaceutical composition according to claims 17, or 18 which comprises up to 30% weight of a water-immiscible solvent.

20. The sterile, pharmaceutical composition according to claim 19 which comprises from about 10% to about 20% weight of a water-immiscible solvent.

21. The sterile, pharmaceutical composition according to claims 17, or 18 wherein the water-immiscible solvent is a vegetable oil or ester of a fatty acid.

22. The sterile, pharmaceutical composition according to claim 21 wherein the vegetable oil is soybean oil.

23. The sterile, pharmaceutical composition according to claims 17, or 18 wherein the surfactant is a naturally occurring phosphatide.

24. The sterile, pharmaceutical composition according to claim 23 wherein the phosphatide is egg phosphatide or soy phosphatide.

25. The sterile, pharmaceutical composition according to claims 17, or 18 wherein the pH is between about4.5 to about 6,4.

26. The sterile, pharmaceutical composition according to claim 25 wherein sodium hydroxide is present.

27. The sterile, pharmaceutical composition according to claims 17, or 18 which is isotonic with blood.

28. The sterile, pharmaceutical composition according to claim 27 which is made isotonic with blood by incorporation of glycerin.

29. The sterile, pharmaceutical composition according to claims 17, or 18 which comprises from about 1% to about 2% weight propofol.

30. The sterile, pharmaceutical composition according to claim 29 which comprises about 1% weight propofol.

31. The sterile, pharmaceutical composition according to claim 29 which comprises about 2% weight propofol.

32. The sterile, pharmaceutical composition of claim 17 wherein the sulfite is selected from the group consisting of sodium metabisulfite, sodium sulfite, sodium bisulfite, potassium metabisulfite, and potassium sulfite.

33. The pharmaceutical composition of claim 32 wherein said sulfite is sodium metabisulfite.

34. A sterile, pharmaceutical composition for parenteral administration which comprises by weight:
   a. about 1% propofol;
   b. about 10% soybean oil;
   c. about 2.25% glycerin;
   d. about 1.2% egg-yolk phospholipid;
   e. about 0.025% of any of sodium metabisulfite, sodium bisulfite, sodium sulfite, potassium metabisulfite, or potassium sulfite, or any combination thereof;
   f. sodium hydroxide; and
   g. water to 100%.

35. A sterile, pharmaceutical composition for parenteral administration which comprises by weight:
   a. about 2% propofol;
   b. about 10% soybean oil;
   c. about 2.25% glycerin;
   d. about 1.2% egg-yolk phospholipid;
   e. about 0.025% of any of sodium metabisulfite, sodium bisulfite, sodium sulfite, potassium metabisulfite, or potassium sulfite, or any combination thereof;
   f. sodium hydroxide; and
   g. water to 100%.

36. A sterile, pharmaceutical composition for parenteral administration which comprises an oil-in-water emulsion in which propofol is emulsified with water, and is stabilized by means of a surfactant, and which further comprises an amount of sulfite sufficient to prevent a no more than 10-fold increase in the growth of each of *Staphylococcus aureus* (ATCC 6538), *Escherichia coli* (ATCC 8739), *Pseudomonas æruginosa* (ATCC 9027), and *Candida albicans* (ATCC 10231) for at least 24 h as measured by a test wherein a washed suspension of each organism is added to a separate aliquot of said composition at approximately 50 colony-forming units per mL and incubated at a temperature in the range 30–35° C. and are tested for viable counts of said organisms after 24 h and wherein said amount of sulfite is less than 0.1% weight of said composition.

37. A sterile, total-parenteral-nutrition composition for parenteral administration which comprises an oil-in-water emulsion in which a lipid is emulsified with water and which further comprises an amount of sulfite sufficient to prevent a no more than 10-fold increase in the growth of each of *Staphylococcus aureus* (ATCC 6538), *Escherichia coli* (ATCC8739), *Pseudomonas æruginosa* (ATCC 9027), and *Candida albicans* (ATCC 10231) for at least 24 h as measured by a test wherein a washed suspension of each organism is added to a separate aliquot of said composition at approximately 50 colony-forming units per mL and incubated at a temperature in the range 30–35° C. and are tested for viable counts of said organisms after 24 h, wherein said amount of sulfite is less than 0.1% weight of said composition.

38. A sterile, pharmaceutical composition for parenteral administration which comprises an oil-in-water emulsion in which a lipophilic pharmaceutical or therapeutic agent is dissolved in a water-immiscible solvent, is emulsified with water, and is stabilized by means of a surfactant, and which further comprises an amount of sulfite sufficient to prevent a no more than 10-fold increase in the growth of each of *Staphylococcus aureus* (ATCC 6538), *Escherichia coli* (ATCC 8739), *Pseudomonas æruginosa* (ATCC 9027), and *Candida albicans* (ATCC 10231) for at least 24 h as measured by a test wherein a washed suspension of each organism is added to a separate aliquot of said composition at approximately 50 colony-forming units per mL and incubated at a temperature in the range 30–35° C. and are tested for viable counts of said organisms after 24 h, and wherein said amount of sulfite is less than 0.1% weight of said composition.

39. A sterile, pharmaceutical composition for parenteral administration which comprises an oil-in-water emulsion in which a lipophilic pharmaceutical or therapeutic agent is emulsified with water and is stabilized by means of a surfactant, and which further comprises an amount of sulfite sufficient to prevent a no more than 10-fold increase in the growth of each of *Staphylococcus aureus* (ATCC 6538), *Escherichia coli* (ATCC 8739), *Pseudomonas æruginosa* (ATCC 9027), and *Candida albicans* (ATCC 10231) for at least 24 h as measured by a test wherein a washed suspension of each organism is added to a separate aliquot of said composition at approximately 50 colony-forming units per mL and incubated at a temperature in the range 30–35° C. and are tested for viable counts of said organisms after 24 h, and wherein said amount of sulfite is less than 0.1% weight of said composition.

40. A method for inducing anesthesia comprising parenteral administration of a composition which comprises an oil-in-water emulsion in which propofol is dissolved in a water-immiscible solvent, is emulsified with water, and is stabilized by means of a surfactant, and which further comprises an amount of sulfite sufficient to prevent a no more than 10-fold increase in the growth of each of *Staphylococcus aureus* (ATCC 6538), *Escherichia coli* (ATCC 8739), *Pseudomonas æruginosa* (ATCC 9027), and *Candida albicans* (ATCC 10231) for at least 24 h as measured by a test wherein a washed suspension of each organism is added to a separate aliquot of said composition at approximately 50 colony-forming units per mL and incubated at a temperature in the range 30–35° C. and are tested for viable counts of said organisms after 24 h, and wherein said amount of sulfite less than 0.1% weight of said composition.

41. The method for inducing anesthesia according to claim 40 wherein the method of administration is by intravenous injection.

42. The method for inducing anesthesia according to claim 41 wherein the injection is by a single injection.

43. The method for inducing anesthesia according to claim 41 wherein the injection is by multiple injections.

44. The method for inducing anesthesia according to claim 40 wherein the method of administration is by continuous infusion.

45. A method of maintaining anesthesia comprising parenteral administration of a composition which comprises an oil-in-water emulsion in which propofol is dissolved in a water-immiscible solvent, is emulsified with water, and is stabilized by means of a surfactant, and which further comprises an amount of sulfite sufficient to prevent a no more than 10-fold increase in the growth of each of *Staphylococcus aureus* (ATCC 6538), *Escherichia coil* (ATCC 8739), *Pseudomonas æruginosa* (ATCC 9027), and *Candida albicans* (ATCC 10231) for at least 24 h as measured by a test wherein a washed suspension of each organism is added to a separate aliquot of said composition at approximately 50 colony-forming units per mL and incubated at a temperature in the range 30–35° C. and are tested for viable counts of said organisms after 24 h, and wherein said amount of sulfite is less than 0.1% weight of said composition.

46. The method of maintaining anesthesia according to claim 45 wherein the method of administration is by multiple bolus injections.

47. The method of maintaining anesthesia according to claim 45 wherein the method of administration is by continuous infusion.

48. A method of sedation comprising parenteral administration of a composition which comprises an oil-in-water emulsion in which propofol is dissolved in a water-immiscible solvent, is emulsified with water, and is stabilized by means of a surfactant, and which further comprises an amount of sulfite sufficient to prevent a no more than 10-fold increase in the growth of each of *Staphylococcus aureus* (ATCC 6538), *Escherichia coli* (ATCC 8739), *Pseudomonas æruginosa* (ATCC 9027), and *Candida albicans* (ATCC 10231) for at least 24 h as measured by a test wherein a washed suspension of each organism is added to a separate aliquot of said composition at approximately 50 colony-forming units per mL and incubated at a temperature in the range 30–35° C. and are tested for viable counts of said organisms after 24 h, and wherein said amount of sulfite is lest than 0.1% weight of said composition.

49. The method of sedation according to claim 48 wherein the method of administration is by continuous infusion.

50. The process for the manufacture of compositions of claims 17, 34, or 35 comprising the steps of:
 a. Degassing the water for injection (WFI) by sparging with nitrogen;
 b. Preparing an aqueous phase by adding glycerin and sodium hydroxide to about 80% WFI in a compounding tank while maintaining the temperature at approximately 40° C.;
 c. Adding the egg-yolk phospholipid to said aqueous phase;
 d. Homogenizing said aqueous phase;
 e. Filtering said aqueous phase through a 5.0 μm filter;
 f. Preparing an oil phase by dissolving propofol in soybean oil;

g. Filtering said oil phase through a 0.45 μm filter;

h. Combining and homogenizing said aqueous and oil phases;

i. Adding a solution of any of sodium metabisulfite, sodium bisulfite, sodium sulfite, potassium metabisulfite, or potassium sulfite, or any combination thereof, dissolved in WFI near the end of the homogenization step;

j. Adding sodium hydroxide or hydrochloric acid solution to adjust the pH;

k. Adjusting to volume with SWFI;

l. Microfluidizing the crude emulsion to the target globule size and particle size distribution while maintaining the temperature at about 30° C.;

m. Filtering the propofol oil-in-water emulsion into a filling vessel;

n. Filling and sealing containers under nitrogen; and o. Autoclaving said containers.

51. The method of claim 50 wherein all of said steps are performed under an inert atmosphere.

52. The method of claim 51 wherein said inert atmosphere is a nitrogen atmosphere.

53. The sterile pharmaceutical composition of claim 34 wherein the sulfite in part e. is sodium metabisulfite.

54. The sterile pharmaceutical composition of claim 35 wherein the sulfite in part e. is sodium metabisulfite.

55. The sterile pharmaceutical composition of claims 36, 37, 38, or 39 wherein said sulfite is sodium metabisulfite.

56. The method of claims 41, 45, or 49 wherein said sulfite in said composition is sodium metabisulfite.

57. A sterile, pharmaceutical composition for parenteral administration which comprises an oil-in-water emulsion of propofol and a pharmaceutically acceptable amount of sulfite sufficient to prevent a no more than 10-fold increase in the growth of each of *Staphylococcus aureus* (ATCC 6538), *Escherichia coli* (ATCC 8739), *Pseudomonas ærugi­nosa* (ATCC 9027), and *Candida albicans* (ATCC 10231) for at least 24 h as measured by a test wherein a washed suspension of each organism is added to a separate aliquot of said composition at approximately 50 colony-forming units per mL and incubated at a temperature in the range 30–±° C. and are tested for viable counts of said organisms after 24 h, prepared by a. Performing all steps under an inert atmosphere;

b. Degassing the water for injection (WFI) by sparging with an inert gas;

c. Preparing an aqueous phase by adding an isotonicity agent to WFI in a compounding tank while maintaining the temperature at approximately 40° C.;

d. Adding a surfactant to said aqueous phase;

e. Homogenizing said aqueous phase;

f. Filtering said aqueous phase through a 5.0 μm filter;

g. Preparing an oil phase selected from the group consit­ing of propofol, and propofol dissolved in a water immiscible solvent;

h. Filtering said oil phase through a 0.45 μm filter;

i. Combining and homogenizing said aqueous and oil phases;

j. Adding a solution of sulfite dissolved in WFI near the end of the homogenization step;

k. Adding sodium hydroxide or hydrochloric acid solution to adjust the pH;

l. Adjusting to volume with SWFI;

m. Microfluidizing the crude emulsion to the target glob­ule size and particle size distribution while maintaining the temperature at about 30° C.;

n. Filtering the propofol oil-in-water emulsion into a filling vessel;

o. Filling and sealing containers under an inert gas; and p. Autoclaving said containers.

58. A sterile, pharmaceutical composition according to claim 57 wherein the sulfite is sodium metabisulfite, the water immiscible solvent is soybean oil, the surfactant is egg phosphatide or soy phosphatide, the pH is between about 4.5 to about 6.4, sodium hydroxide is present, and wherein said sterile, pharmaceutical composition is made isotonic with blood by incorporation of glycerin.

59. A sterile, pharmaceutical composition according to claim 58 which is prepared under a nitrogen atmosphere.

60. A sterile, pharmaceutical composition according to claim 57 which comprises by weight:

a. about 1% propofol;

b. about 10% soybean oil;

c. about 2.25% glycerin;

d. about 1.2% egg-yolk phospholipid;

e. about 0.025% sodium metabisulfite;

f. sodium hydroxide;

g. water to 100%.

61. A sterile, pharmaceutical composition according to claim 57 which comprises by weight:

a. about 2% propofol;

b. about 10% soybean oil;

c. about 2.25% glycerin;

d. about 1.2% egg-yolk phospholipid;

e. about 0.025% sodium metabisulfite;

f. sodium hydroxide;

g. water to 100%.

62. The process of claim 50 wherein the sulfite added in step i. is sodium metabisulfite.

63. A method according to claim 45 wherein said sulfite is sodium metabisulfite, said immiscible solvent is soybean oil, said surfactant is selected from the group consisting of egg phosphatide and soy phosphatide, the pH of said oil-in-water emulsion is between about 4.5 to about 6.4, wherein said composition is made isotonic with blood by incorpo­ration of glycerin.

64. A method according to claim 63 wherein said com­position comprises about 1% weight propofol.

65. A method according to claim 63 wherein said com­position comprises about 2% weight propofol.

66. The methods of claims 40, 45, and 48 wherein said sulfite is selected from the group consisting of sodium metabisulfite, sodium sulfite, sodium bisulfite, potassium sulfite, potassium bisulfite, and potassium metabisulfite, and wherein the amount of said sulfite is in the range of about 0.0073% to less than 0.1% weight.

67. The method of claim 66 wherein said sulfite is sodium metabisulfite.

68. A method according to claim 67 wherein the amount of said sodium metabisulfite is about 0.025% weight.

69. A method according to claim 67 wherein said com­position comprises up to 30% weight of a water-immiscible solvent.

70. A method according to claim 69 wherein said com­position comprises from about 10% to about 20% weight of a water-immiscible solvent.

71. A method according to claim 67 wherein the water-immiscible solvent is a vegetable oil or ester of a fatty acid, and wherein said surfactant is a naturally occurring phosphatide.

72. A method according to claim 71 wherein the vegetable oil is soybean oil, and wherein said phosphatide is egg phosphatide or soy phosphatide.

73. A method according to claim 67 wherein the pH of the emulsion is between about 4.5 to about 6.4.

74. A method according to claim 67 wherein said composition is isotonic with blood.

75. A method according to claim 74 wherein said composition is made isotonic with blood by incorporation of glycerin.

76. A method according to claim 67 wherein said composition comprises from about 1% to about 2% weight propofol.

77. A method according to claim 76 wherein said composition comprises about 1% weight propofol.

78. A method according to claim 76 wherein said composition comprises about 2% weight propofol.

79. A method of inducing anesthesia comprising the parenteral administration of a sterile pharmaceutical composition which comprises by weight:

a. about 1% propofol;

b. about 10% soybean oil;

c. about 2.25% glycerin;

d. about 1.2% egg-yolk phospholipid;

e. about 0.025% sodium metabisulfite;

f. sodium hydroxide;

g. water to 100%.

80. A method of inducing anesthesia comprising the parenteral administration of a sterile pharmaceutical composition which comprises by weight:

a. about 2% propofol;

b. about 10% soybean oil;

c. about 2.25% glycerin;

d. about 1.2% egg-yolk phospholipid;

e. about 0.025% sodium metabisulfite;

f. sodium hydroxide;

g. water to 100%.

\* \* \* \* \*